(12) United States Patent
Emori et al.

(10) Patent No.: US 7,655,430 B2
(45) Date of Patent: Feb. 2, 2010

(54) METHOD FOR ANALYZING RESIDUAL AGRICULTURAL CHEMICAL

(75) Inventors: Takayuki Emori, Chiyoda-ku (JP); Koshiro Kajiyama, Chiyoda-ku (JP); Junichi Kato, Higashi-hiroshima (JP)

(73) Assignees: Satake Corporation, Tokyo (JP); Junichi Kato, Higashi-hiroshima-shi (JP)

( * ) Notice: Subject to any disclaimer, the term of this patent is extended or adjusted under 35 U.S.C. 154(b) by 599 days.

(21) Appl. No.: 11/088,871

(22) Filed: Mar. 25, 2005

(65) Prior Publication Data

US 2005/0214887 A1    Sep. 29, 2005

(30) Foreign Application Priority Data

Mar. 25, 2004    (JP)    ............... 2004-089137

(51) Int. Cl.
*C12Q 1/00* (2006.01)
*C12Q 1/06* (2006.01)
*C12Q 1/46* (2006.01)
*C12Q 1/48* (2006.01)
*C12Q 3/00* (2006.01)
*C12Q 1/34* (2006.01)
*C12Q 1/26* (2006.01)

(52) U.S. Cl. .......................................... 435/15; 435/10
(58) Field of Classification Search ................. 504/100; 435/15, 10
See application file for complete search history.

(56) References Cited

U.S. PATENT DOCUMENTS

| | | | | |
|---|---|---|---|---|
| 4,830,513 | A | * | 5/1989 | Grego ......................... 374/131 |
| 4,830,856 | A | * | 5/1989 | Peppers ....................... 424/449 |
| 5,302,513 | A | * | 4/1994 | Miike et al. .................... 435/15 |
| 5,302,514 | A | * | 4/1994 | Tokutake et al. .............. 435/22 |

FOREIGN PATENT DOCUMENTS

| | | |
|---|---|---|
| JP | 9-107992 | 4/1997 |
| JP | 2003-298 | 1/2003 |

OTHER PUBLICATIONS

EnviroLogix Cholinesterase Screening Test Application Sheet for the Detection of Organophosphate and Carbamate Residues in Dried Vine and Tree Fruit [revised on Sep. 9, 2003]. Retrieved from the Internet: < URL: http://www.envirologix.com/library/ep014appguide.pdf EnviroLogix%20Cholinesterase%20Screening%20Test; pp. 1-6.*
Umetsh, Journal of Pesticide Science, 1986: vol. 11, No. 3: abstract.*
Syed et al. Journal of Environmental Science and Health. Part B, Pesticides, food contaminants, and agricultural waters, Aug. 1992; 27(4): 347-354.*
Sivori et al., Mem Inst Oswaldo Cruz, Rio de Janeiro, vol. 92(6)L 797-802,Nov./Dec. 1997.*
Winterlin et al.Journal of Agriculture Food Chemistry, vol. 16, No. 5, May 1968: 808-812.*

* cited by examiner

*Primary Examiner*—Johann R Richter
*Assistant Examiner*—Courtney Brown
(74) *Attorney, Agent, or Firm*—Oblon, Spivak, McClelland, Maier & Neustadt, L.L.P.

(57) ABSTRACT

The present invention relates to a method for analyzing residual agricultural chemicals which comprises the steps of acting a reduced glutathione as a reactive substrate and a glutathione transferase serving as a catalyst for the reaction on a carbofuran derivative or a methomyl derivative as a carbamate type agricultural chemical of a new series to thus derivatize the agricultural chemical into a substance having a high choline esterase-inhibitory activity; reacting the substances formed through the derivatization reaction with a choline esterase; and then detecting the presence of the agricultural chemical as the new series of carbamate type one included in a sample to be examined on the basis of the changes in the choline esterase activity thus detected. The method of the present invention may serve as a powerful tool for the detection of the residual agricultural chemicals in grains such as rice and the detection of the content of agricultural chemicals remaining in agricultural products such as vegetables and fruits.

16 Claims, 5 Drawing Sheets

FIG.2

10 mL OF 0.02M MES BUFFER
SOLUTION (pH 6.0)
 │
 ├── CARBOFURAN DERIVATIVE
 │   (CARBOSULFAN)
 │
 ├── $5 \times 10^{-5}$ M-REDUCED GLUTATHIONE (GSH)
 │
 ├── 0.025 U/mL-GLUTATHIONE
 │   TRANSFERASE (GST)
 ▼
ALLOWING THE MIXTURE TO STAND OVER
AT LEAST 30 MINUTES (CONVERSION)
 │
 ├── 10 mL
 │   (0.2M-PHOSPHATE BUFFER SOLUTION
 │   (pH 7.6) + 0.2M POTASSIUM CHLORIDE)
 │
 ├── 0.01 U/mL-CHOLINE ESTERASE (ChE)
 │
 ├── 1 U/mL-CHOLINE OXIDASE (ChOD)
 ▼
ALLOWING THE MIXTURE TO STAND OVER
AT LEAST 60 MINUTES (CONVERSION)
 │
 ├── $2 \times 10^{-4}$ M-ACETYLCHOLINE (ACh)
 ▼
DETERMINATION OF HYDROGEN
PEROXIDE CONTENT

● : CARBOSULFAN (CONTAINING GST AND GSH)

◯ : CARBOSULFAN (FREE OF GST AND GSH)

△ : CARBOFURAN

● : CALIBRATION CURVE OBTAINED WHEN ADDING 20 ppb OF BENFURACARB TO A TEST SAMPLE (BROWN RICE) AND THEN RECOVERING THE SAME

○ : CALIBRATION CURVE FOR BENFURACARB

METHOD FOR ANALYZING RESIDUAL AGRICULTURAL CHEMICAL

BACKGROUND OF THE INVENTION

The present invention relates to a method for detecting or analyzing an agricultural chemical possibly remaining in farm products, for instance, grains such as rice; vegetables; and fruits and more particularly to a method for analyzing such residual agricultural chemicals present in farm products, which permits the detection of, in particular, new series of carbamate type agricultural chemicals.

The inventors of this invention have previously proposed a method for detecting residual agricultural chemicals, which permits the simultaneous detection of an organophosphorus agricultural chemical and a carbamate type agricultural chemical (see the Patent Reference 1 given later).

This method would allow, with ease, the division of the agricultural chemicals remaining in a sample to be analyzed into organophosphorus type ones and carbamate type ones and the simultaneous detection of these different kind agricultural chemicals and the method comprises the steps of admixing the sample with a mixed solution containing a carboxyl esterase and a choline esterase to thus react them; hydrolyzing a substrate specific to the carboxyl esterase and a substrate specific to the choline esterase using the solution obtained after the foregoing reaction to thus make the hydrolyzates of these substrates develop colors, while adding, to the system, a color former or a coupler to the hydrolyzates or selecting the foregoing substrates in such a manner that they can form hydrolyzates capable of developing colors in themselves; and simultaneously detecting spectral changes of a plurality of light rays having different wavelengths.

Because of the foregoing constitution, this method permits, with ease, the simultaneous discrimination and detection of an organophosphorus agricultural chemical and a carbamate type agricultural chemical possibly present in a sample to be analyzed (or a test sample). More specifically, this method is characterized by hydrolyzing a substrate specific to the carboxyl esterase and a substrate specific to the choline esterase; simultaneously detecting absorption spectra ascribable to the decomposition of these two kinds of substrates using a spectrophotometer which can simultaneously irradiate the hydrolyzed system with a plurality of light rays having different wavelengths and which permits the detection of any spectral change of the system with the elapse of time; calculating the reaction rates of each enzyme-catalyzed reaction according to an appropriate arithmetic treatment; and thus discriminatively detecting the organophosphorus agricultural chemical and the carbamate type agricultural chemical present in the sample on the basis of the changes in the reaction rates thus determined.

The foregoing method permits the discrimination and detection of a group of organophosphorus agricultural chemicals and that of carbamate type ones, but the precision of the analysis would be reduced depending on the kinds of agricultural chemicals and some of carbamate type ones hardly undergo inhibition of enzymes and this would make the precision of the analysis insufficient.

In this connection, it has been known that the carbamate type insecticides show their insecticidal action through the reduction of the action of a choline esterase which governs or manages the nervous systems of injurious insects. The carbamate type insecticides registered long ago suffer from such a problem that they are excellent in the fast-acting properties, but they are insufficient in the long-acting properties. Moreover, it had been desired for the improvement of the foregoing carbamate type insecticides in the latter half of 1970s because of the development or emergence of bacteria resistant to these insecticides in the bodies of injurious insects to be controlled. Under such circumstances, there have been registered, as new series of carbamate type agricultural chemicals, the following six components: carbofuran analogues (bendiocarb), carbofuran derivatives (carbosulfan, furathiocarb and benfuracarb) and methomyl derivatives (thiodicarb and alanicarb) since 1980s while taking the foregoing problems into consideration.

The foregoing new series of carbamate type agricultural chemicals except for bendiocarb are agricultural chemicals which are so designed that each of them is converted into carbofuran or methomyl having a greater activity of inhibiting the choline esterase activity due to the natural metabolic action after the spray thereof on farm products and then they gradually show their efficacy because of the formation of such effective components.

The carbofuran derivatives among the foregoing new series of carbamate type agricultural chemicals have structures (carbofuran-S—R) in which carbofuran having a strong activity of inhibiting choline esterase activity is linked to the other constituent molecule through a sulfide bond and the methomyl derivatives likewise have structures similar thereto (methomyl-S—R). These agricultural chemicals are ones which are so designed that they suffer natural metabolic actions after the spray thereof on farm products and as a result, they are gradually converted into carbofuran or methomyl, to thus show their insecticidal actions. In other words, the carbofuran derivatives and the methomyl derivatives show only weak abilities to inhibit the choline esterase and accordingly, they have never provided any satisfactory detection sensitivity with respect to the standard level of the residual agricultural chemical acceptable for farm products.

Patent Reference 1: Japanese Un-Examined Patent Publication 2003-298

SUMMARY OF THE INVENTION

It is generally an object of the present invention to solve the foregoing problems associated with the conventional techniques and more specifically to provide a method for analyzing residual agricultural chemicals possibly present in farm products, which permits the detection of new series of carbamate type agricultural chemicals contained in a sample to be examined at a high detection sensitivity.

Accordingly, the present invention herein provides a method for detecting or analyzing residual agricultural chemicals detailed below:

1. A method for analyzing residual agricultural chemicals which comprises the steps of acting a reduced glutathione as a reactive substrate and a glutathione transferase serving as a catalyst for the reaction on a carbofuran derivative or a methomyl derivative as a new series of carbamate type agricultural chemical to thus derivatize the agricultural chemical into a substance having a high choline esterase-inhibitory activity; reacting the substances formed through the derivatization reaction with a choline esterase; and then detecting the presence of the agricultural chemical of the new series of carbamate type one included in a sample to be examined on the basis of the changes in the choline esterase activity thus detected.

2. The method for analyzing residual agricultural chemicals as set forth in the foregoing item 1, wherein the carbamate type agricultural chemical of such new series included in the sample to be examined is detected after adding, to the sample, a chelating agent having a strong ability to form a complex with metal ions present in the sample in order to alleviate an influence thereof which may be obstructive to the derivatization reaction.
3. The method as set forth in the foregoing item 1 or 2, wherein the carbofuran derivative is carbosulfan, furathiocarb or benfuracarb.
4. The method as set forth in the foregoing item 1 or 2, wherein the methomyl derivative is thiodicarb or alanicarb.
5. The method as set forth in the foregoing item 2, wherein the chelating agent is at least one member selected from the group consisting of polyaminocarboxylic acids and oxycarboxylic acids.
6. The method as set forth in the foregoing item 2, wherein the chelating agent is EDTA or citric acid.
7. The method as set forth in the foregoing item 1 or 2, wherein the sample to be examined is a farm product.
8. The method as set forth in the foregoing item 1 or 2, wherein the sample to be examined is rice, a vegetable or a fruit.
9. The method as set forth in the foregoing item 1 or 2, wherein the sample to be examined is unmilled rice (brown rice).

The present invention is thus characterized by derivatizing a carbofuran derivative or a methomyl derivative, as a carbamate type agricultural chemical of the foregoing new series, present in a sample to be analyzed while making use of the catalytic action of a glutathione transferase; reacting the resulting products of the derivatization reaction with a choline esterase; and then detecting the carbamate type agricultural chemical of the new series on the basis of the detected changes in the choline esterase activity. In a preferred embodiment, the present invention is characterized in that the carbamate type agricultural chemical of the new series included in the sample to be examined is detected after adding, to the sample, a chelating agent having a strong ability to form a complex with metal ions possibly present in the test sample in order to alleviate an influence of the metal ions serving as obstructive substances in the derivatization reaction which makes use of the catalytic action of the foregoing glutathione transferase.

As has been discussed above, in the method of the present invention, a carbofuran derivative or a methomyl derivative included in a sample to be analyzed is derivatized to thus convert the same into a substance having a high activity of inhibiting the activity of a choline esterase and the detection of the foregoing agricultural chemical is carried out after the resulting derivatized products are reacted with the choline esterase. Accordingly, the method of the present invention would permit the detection, at a satisfactory detection sensitivity, of the carbofuran derivatives or methomyl derivatives which have only weak choline esterase-inhibitory activity and provide unsatisfactory detection sensitivity.

In the method of the present invention, the foregoing carbamate type agricultural chemical present in a sample to be analyzed is derivatized after the addition of a chelating agent having a strong ability of forming a complex with metal ions to the sample, the products obtained through the derivatization reaction is reacted with a choline esterase and then the agricultural chemical is detected. Accordingly, the method of the invention permits the smooth derivatization of the foregoing new series of carbamate type agricultural chemicals and the detection thereof with a sufficiently high precision as compared with the standard level of the residual agricultural chemical.

BRIEF DESCRIPTION OF THE DRAWINGS

The present invention will hereunder be described in more detail with reference to the accompanying drawings, wherein
FIG. 2 is a flow diagram for the illustration of the derivatization of carbosulfan.

BEST MODE FOR CARRYING OUT THE INVENTION

The present invention will hereunder be described in more detail while taking the best mode for carrying out the invention by way of example. In this connection, FIG. 1 is a schematic diagram for generally illustrating the method for analyzing agricultural products to inspect for the presence of a residual agricultural chemical therein according to the present invention.

Figure 1:
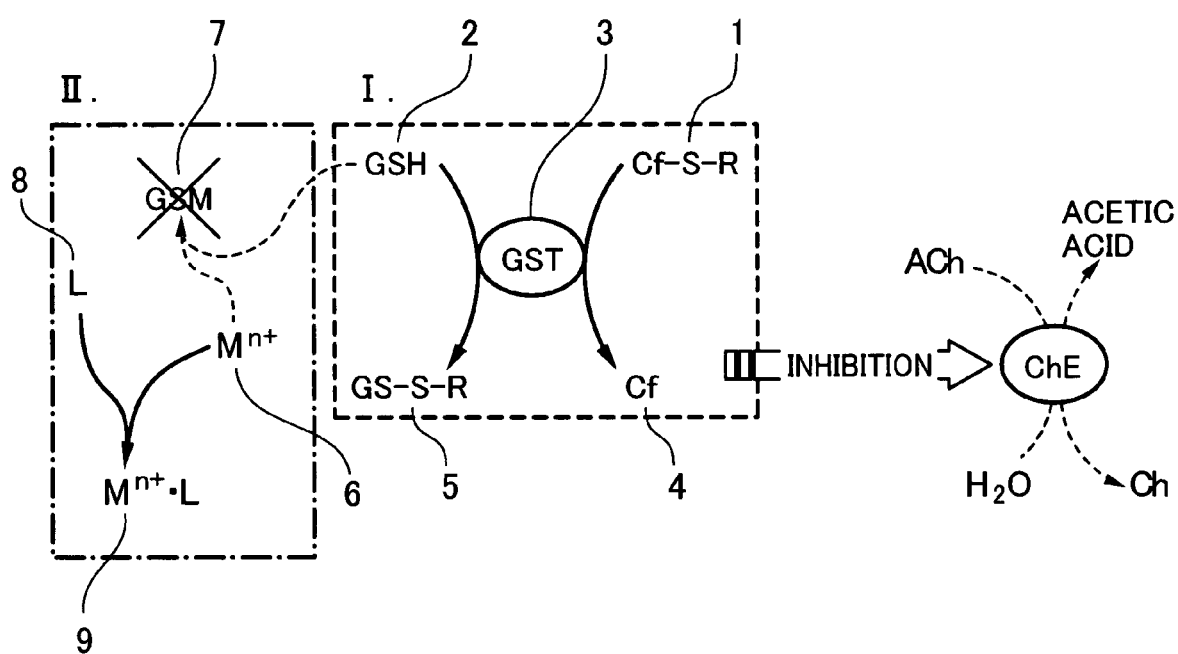
FIG. 1 is a schematic diagram showing the derivatization of a carbofuran derivative into carbofuran and a reaction for alleviating an influence of metal ions which may serve as substances obstructive to the derivatization.

First of all, the region I as shown in FIG. 1, (the region enclosed by four broken lines) will be detailed below. A carbofuran derivative (Cf—S—R) (1) is reacted with a reduced glutathione (GSH) (2) in the presence of a glutathione transferase (GST) (3) as a catalyst to thus convert the carbofuran derivative (Cf—S—R) (1) into carbofuran (Cf) (4). An oxidized glutathione (G-S—S—R) (5) is formed as a by-product during the derivatization reaction.

The foregoing reaction sufficiently proceeds at a temperature ranging from 10 to 40° C. for about 5 to 60 minutes. The pH value of the reaction liquid is usually in the range of from 5.0 to 8.5 and preferably 6.0 to 7.0.

The amount of the enzyme, glutathione transferase (GST), in general ranges from 0.003 to 0.1 U/mL and preferably 0.01 to 0.05 U/mL.

In addition, the concentration of the reduced glutathione (GSH) herein used is usually in the range of from $10^{-6}$ to $10^{-4}$ M and preferably $10^{-5}$ to $5 \times 10^{-5}$ M.

Next, the region II as shown in FIG. 1, (the region surrounded by four alternate long and short dashed lines) will be detailed below. The principal object of this reaction is to alleviate an influence of metal ions $M^{n+}$ (6) included in the sample to be examined on the reduced glutathione (GSH) (2) used in the foregoing derivatization reaction. The foregoing derivatization reaction should be conducted after the completion of the following reactions: A chelating agent (L) (8) having a strong ability of forming a complex with metal ions $M^{n+}$ (6) included in the test sample is added to the test sample to thus form a complex $M^{n+} \cdot L$ (9). In other words, this reaction would inhibit the formation of a reaction product (GSM) (7) between the metal ions $M^{n+}$ (6) and the reduced glutathione (GSH) (2) and this consequently permits the alleviation of an influence of the metal ions $M^{n+}$ (6) on the reduced glutathione (GSH) (2) used in the foregoing derivatization reaction.

The foregoing reaction satisfactorily goes on at a temperature ranging from 10 to 40° C. for about 5 to 15 minutes. The pH value of the reaction liquid is usually in the range of from 4.0 to 12.0 and preferably 6.0 to 8.0.

Examples of the foregoing metal ions are those derived from metals such as magnesium, copper and iron.

In addition, as the chelating agents which have high abilities to form complexes with metal ions possibly included in the test samples used in the present invention, there may be listed, for instance, polyaminocarboxylic acids and oxycarboxylic acids. Specific examples of such polyaminocarboxylic acids include EDTA (ethylenediamine-tetraacetic acid), imino-diacetic acid and nitrilo-triacetic acid, while specific examples of such oxycarboxylic acids are citric acid, tartaric acid and oxy-benzoic acid. The concentration of the chelating agent used herein is not restricted to a specific range, but it in general ranges from $10^{-4}$ to $10^{-1}$M and preferably $10^{-3}$ to $10^{-2}$M.

The foregoing glutathione transferase (GST) (3) has a catalytic action such that it can convert a carbofuran derivative or a methomyl derivative into carbofuran or methomyl, respectively while making use of a reduced glutathione (GSH) (2) as a substrate.

The foregoing catalytic action of the glutathione transferase (3) can be represented by the following reaction scheme:

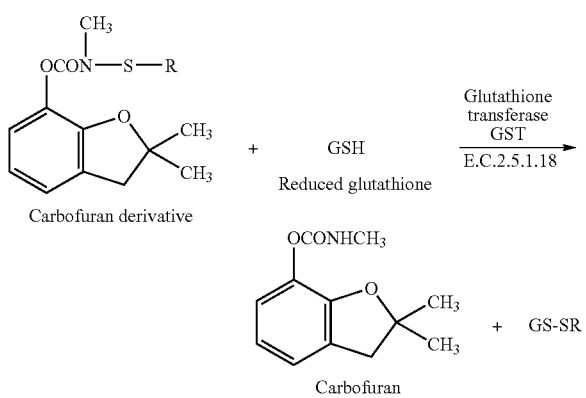

The substituent R appearing in the structural formula of the carbofuran derivative may be those listed in the following Table in which the name of each corresponding agricultural chemical is also given:

| Name of Agricultural Chemical | R |
|---|---|
| carbosulfan | —N[(CH$_2$)$_3$CH$_3$]$_2$ |
| benfuracarb | —N[CH(CH$_3$)$_2$]—(CH$_2$)$_2$CH$_2$CH$_3$ |
| furathiocarb | —N(CH$_3$)—CO$_2$(CH$_2$)$_3$CH$_3$ |

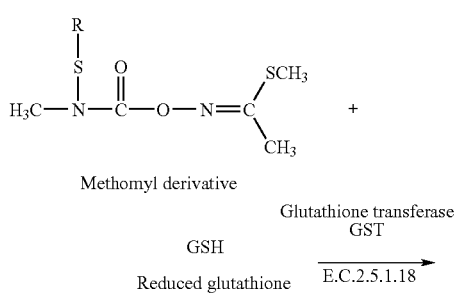

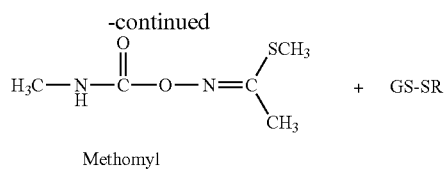

The substituent R appearing in the structural formula of the methomyl derivative may be those listed in the following Table in which the name of each corresponding agricultural chemical is likewise given:

| Name of Agricultural chemical | R |
|---|---|
| alanicarb | —N(CH$_2$—Ph)—(CH$_2$)$_2$CO$_2$CH$_2$CH$_3$ |
| thiodicarb | —N(CH$_3$)—CO$_2$N=C(CH$_3$)—SCH$_3$ |

Ph: phenyl group

As a result, a carbofuran derivative can be converted into carbofuran having a high choline esterase-inhibitory activity and this would permit the detection of the derivative with a high precision. On the other hand, a methomyl derivative can likewise be converted into methomyl having a high choline esterase-inhibitory activity and the derivative may likewise be detected with a high precision.

Moreover, the foregoing chelating agent L (8) is added to a test sample prior to the derivatization reaction of a desired agricultural chemical. This permits the conversion of metal ions $M^{n+}$ (6), which may interfere with the derivatization reaction, into a complex $M^+ \cdot L$ (9), which do not affects the derivatization reaction. In other words, the chelating agent L (8) has an effect of inhibiting the formation of a reaction product between the reduced glutathione (GSH) (2) and the metal ions $M^{n+}$ (6).

The foregoing action can be represented by the following reaction scheme:

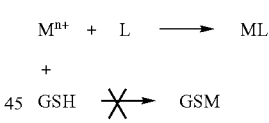

This effect would permit the alleviation of an influence of the metal ions $M^{n+}$ (6) on the reduced glutathione (GSH) (2) used in the foregoing derivatization reaction and the smooth progress of the derivatization reaction.

The present invention will hereunder be described in more detail with reference to the following non-limitative Examples, but the present invention is not restricted to these specific Examples at all.

EXAMPLE 1

In this Example, it was intended to confirm the derivatization of carbosulfan (see FIG. 2). Carbosulfan was converted into carbofuran by adding a reduced glutathione (GSH), to a concentration of $5\times10^{-5}$M, and a glutathione-transferase (GST), to a concentration of 0.025 U/mL, to 10 mL of a 0.02M Mes buffer solution (pH 6.0) (2-morpholino-ethane sulfonic acid) containing carbosulfan in a variety of concentrations and then allowing each resulting reaction system to stand over at least 30 minutes.

Then, 10 mL of a solution containing 0.1M phosphate buffer solution (pH 7.6) and 0.2M potassium chloride was added to the foregoing solution which had been allowed to stand, to thus obtain a solution having a volume of 20 mL. Then, to the resulting solution, there were added a choline esterase and a choline oxidase to concentrations of 0.01 U/mL and 0.5 U/mL, respectively and then the resulting mixture was allowed to stand over at least 60 minutes so that these enzymes were brought into contact with the substances obtained through the foregoing conversion of carbosulfan by the action of the reduced glutathione and the glutathione transferase.

After bringing these components into contact with one another by allowing them to stand, acetylcholine was added to a concentration of $2 \times 10^{-4}$M to the foregoing solution and then the amount of hydrogen peroxide generated was determined to thus inspect the solution for the activity to inhibit the choline esterase activity. The same solution free of a carbosulfan was used as a control and this was compared with the solutions, which included carbosulfan in a variety of concentrations, based on the detected inhibitory signals corresponding to the quantities of the resulting hydrogen peroxide. In this connection, the calibration curve for carbosulfan is shown in FIG. 3.

Figure 3:
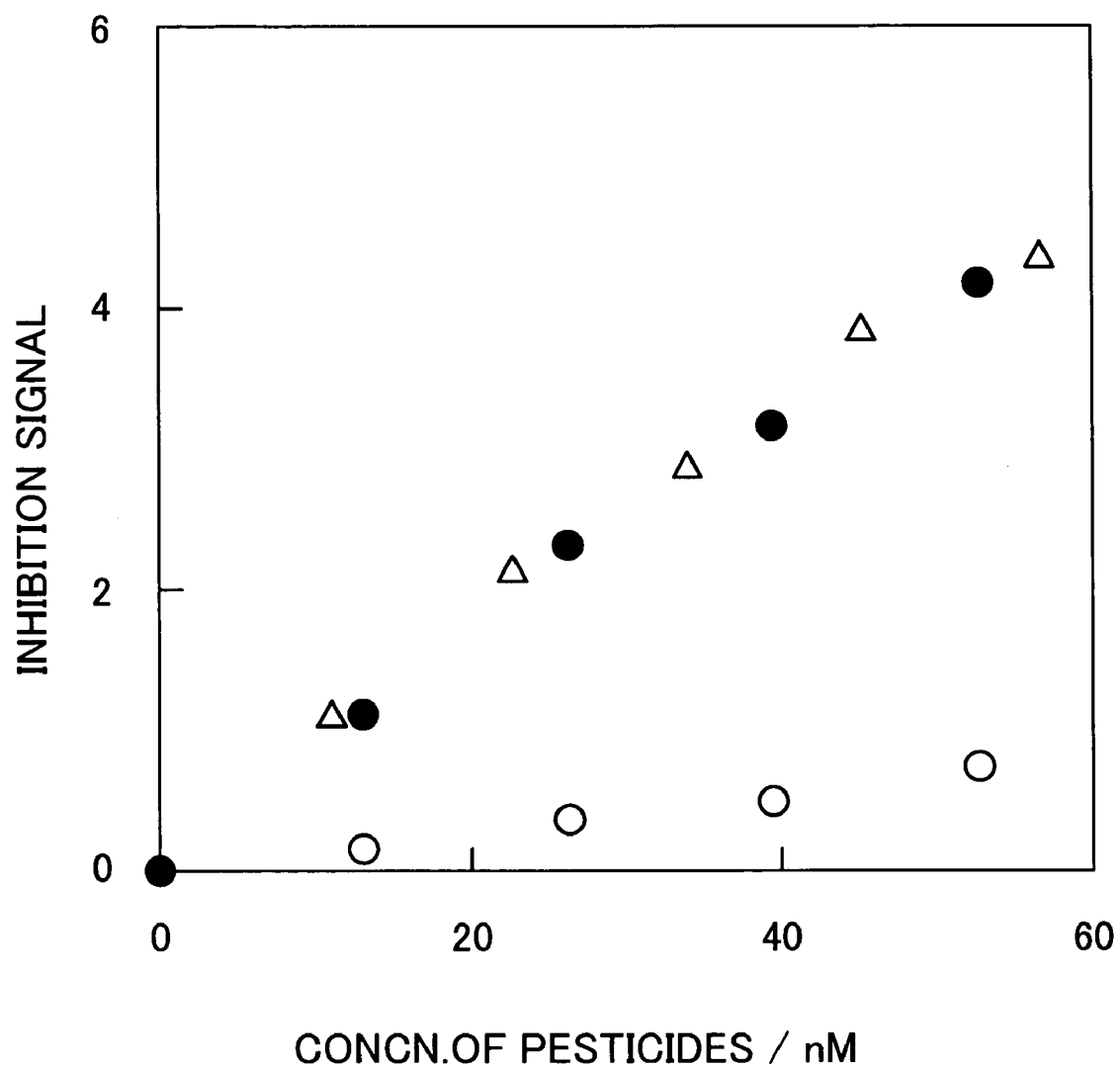
FIG. 3 is a calibration curve for the analysis of carbofuran converted by the action of reducing glutathione and glutathione transferase.
Figure 4:
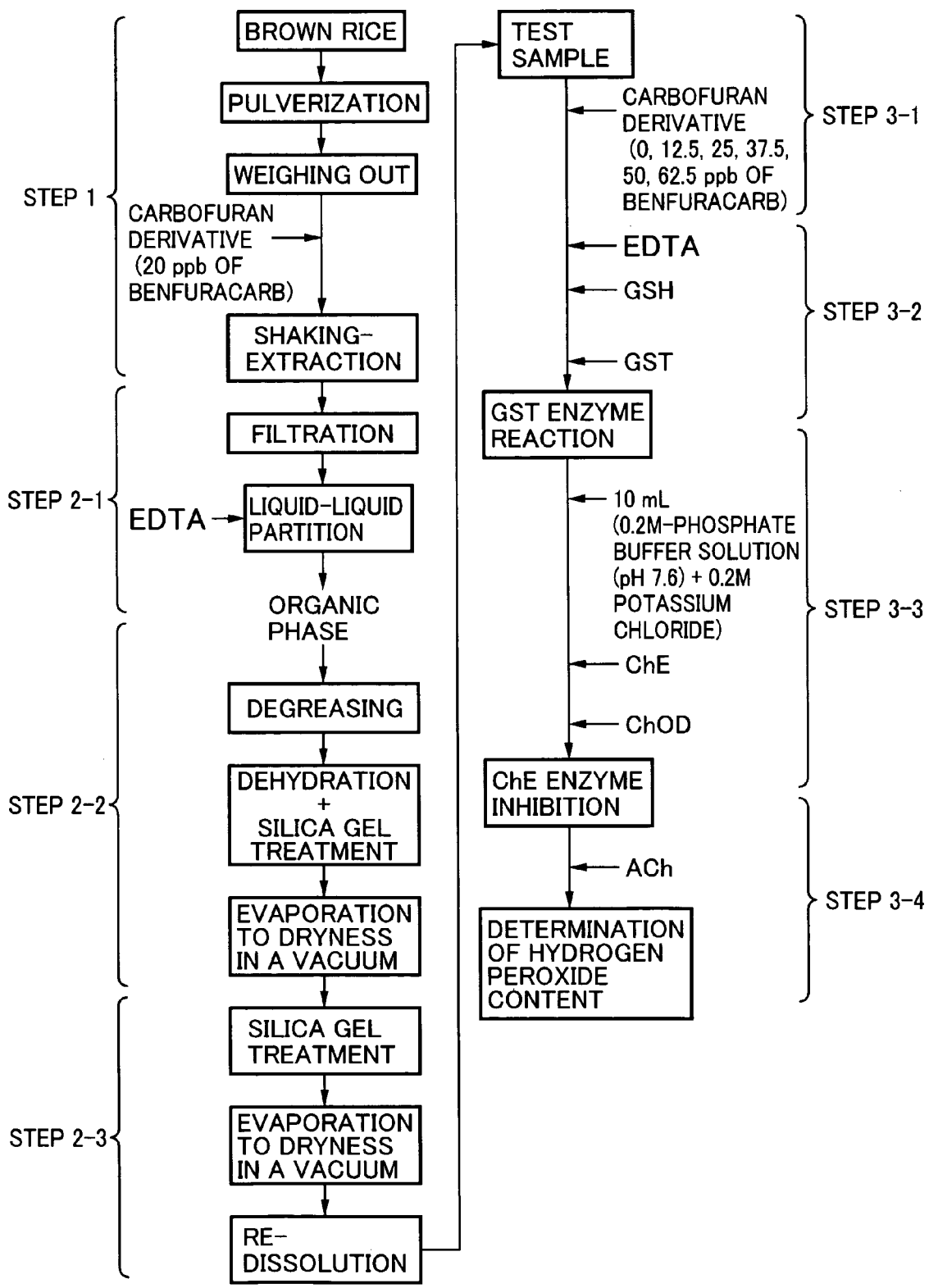
FIG. 4 is a flow diagram for illustrating the analysis of brown rice to check the presence of benfuracarb therein.

In FIG. 3, the concentration of the agricultural chemical is plotted as abscissa and the inhibitory signal as ordinate. The curve represented by filled circles (●) corresponds to the calibration curve obtained by the conversion of a reference material for carbosulfan with a reduced glutathione (GSH) and a glutathione transferase, that represented by open circles (○) is the calibration curve for the reference material of carbosulfan free of any such conversion and that represented by open triangles (Δ) corresponds to the calibration curve for a reference material of carbofuran. The data plotted on FIG. 3 clearly indicate that the reference material of carbosulfan which is free of the foregoing conversion (open circles) (○) shows only a weak inhibitory activity, while the calibration curve observed for the reference material of carbosulfan subjected to such conversion (filled circles) (●) is almost identical to that observed for the reference material of carbofuran (Δ). This clearly indicate that one molecule of carbofuran can be derivatized from one molecule of carbosulfan.

EXAMPLE 2

This Example was conducted to confirm whether the method of the present invention permits the detection or analysis of any benfuracarb as a carbofuran derivative possibly present in brown rice as a test sample, or not, by the addition of benfuracarb to the brown rice and the subsequent recovery thereof. First, brown rice was pulverized, 25 g of the powdered brown rice was weighed out from the powdered brown rice and then benfuracarb was added in a concentration of 20 ppb to 25 g of the powdered brown rice. Thereafter, to 25 g of the powdered brown rice, there were added 25 mL of water and 50 mL of acetonitrile to thus extract the agricultural chemical using a shaker (Step 1).

Then the resulting extract was subjected to suction filtration to remove contaminants of various kinds present therein. The resulting filtrate thus obtained was then subjected to liquid-liquid distribution to remove any water-soluble contaminant and metal ions possibly present therein. This liquid-liquid distribution was carried out by introducing, in advance, 15 mL of a 1M phosphate buffer (pH 7.0) saturated with common salt, 5 g of common salt and 1 mL of 50 mM EDTA solution into a separatory funnel, adding the filtrate, stirring the resulting mixture, allowing the mixture to stand for a while till the mixture was separated into an organic phase and an aqueous phase and then isolating the organic phase. The water-soluble contaminants were preferentially distributed in the aqueous phase mainly comprising the phosphate buffer, while the metal ions were associated with EDTA to form a complex and the complex was preferentially distributed in the aqueous phase and thus these impurities could almost completely be removed from the filtrate (Step 2-1).

Then the foregoing organic phase was treated with ODS (octadecyl silica gel) to remove any lipophilic contaminant (or for the degreasing of the same) and the organic phase was further treated with a column packed with sodium sulfate and silica gel to thus roughly purify the same or remove other contaminants therefrom. The liquid obtained after these treatments was evaporated to dryness under a reduced pressure or the organic solvent was distilled off (Step 2-2).

Further the resulting residue was purified using a silica gel column. More specifically, the residue obtained after the foregoing evaporation of the extract to dryness was dissolved in 5 mL of a solvent mixture comprising ethyl acetate and hexane in a mixing ratio of 3:97 and the resulting solution was loaded on a silica gel column to thus adsorb any contaminant and agricultural chemical present therein on the silica gel. Thereafter, 20 mL of a solvent mixture comprising ethyl acetate and hexane in a mixing ratio of 3:7 was passed through the silica gel column to thus elute the agricultural chemical adsorbed thereon. The resulting elute comprising the foregoing two kinds of mixed solvents was then evaporated to dryness under a reduced pressure or these solvents were distilled off. The residue obtained after the evaporation of the elute to dryness under a reduced pressure was then dissolved in 12.5 mL of a solution comprising 0.02 M Mes buffer solution (pH 6.0) (Step 2-3).

An aliquot (2 mL) was taken from the resulting 12.5 mL of the foregoing solution and then combined with 8 mL of a solution comprising 0.02M Mes buffer solution (pH 6.0) to thus form 10 mL of a mixture which was used in the following step as a test sample. Then benfuracarb as a carbofuran derivative was added to the test sample in a variety of concentrations (Step 3-1).

In this respect, EDTA as a chelating agent having a strong ability to form a complex with metal ions was, in advance, added to the test samples to a concentration of 0.5 mM before the benfuracarb was converted into carbofuran while making use of the action of a reduced glutathione and glutathione transferase in order to alleviate an influence, on the conversion reaction, of the metal ions included in the test samples serving as substances obstructive to the conversion. Then a reduced glutathione and a glutathione transferase were added to each test sample to concentrations of $5 \times 10^{-5}$M and 0.025 U/mL respectively and then each test sample was allowed to stand for a time of not less than 30 minutes to thus convert benfuracarb into carbofuran (Step 3-2).

Then, to each test sample obtained after allowing the same to stand, there were added the same solution, choline esterase and choline oxidase used in Example 1, according to the same procedures used in Example 1 and each resulting mixture was allowed to stand over a time of at least 60 minutes to thus bring the sample into close contact with these enzymes (Step 3-3).

Thereafter, to the test sample thus allowed to stand for the close contact, there was added the same acetylcholine used in Example 1, according to the same procedures used in Example 1 and each test sample was inspected for the amount of hydrogen peroxide generated. The solution free of any agricultural chemical and used in Example 1 was used as a control and this was compared with the test samples, which included benfuracarb in a variety of concentrations, based on the detected inhibitory signals corresponding to the quantities of hydrogen peroxide generated in these test samples (Step 3-4). In this connection, FIG. 5 shows the calibration curve of benfuracarb observed for brown rice as a sample.

Figure 5:
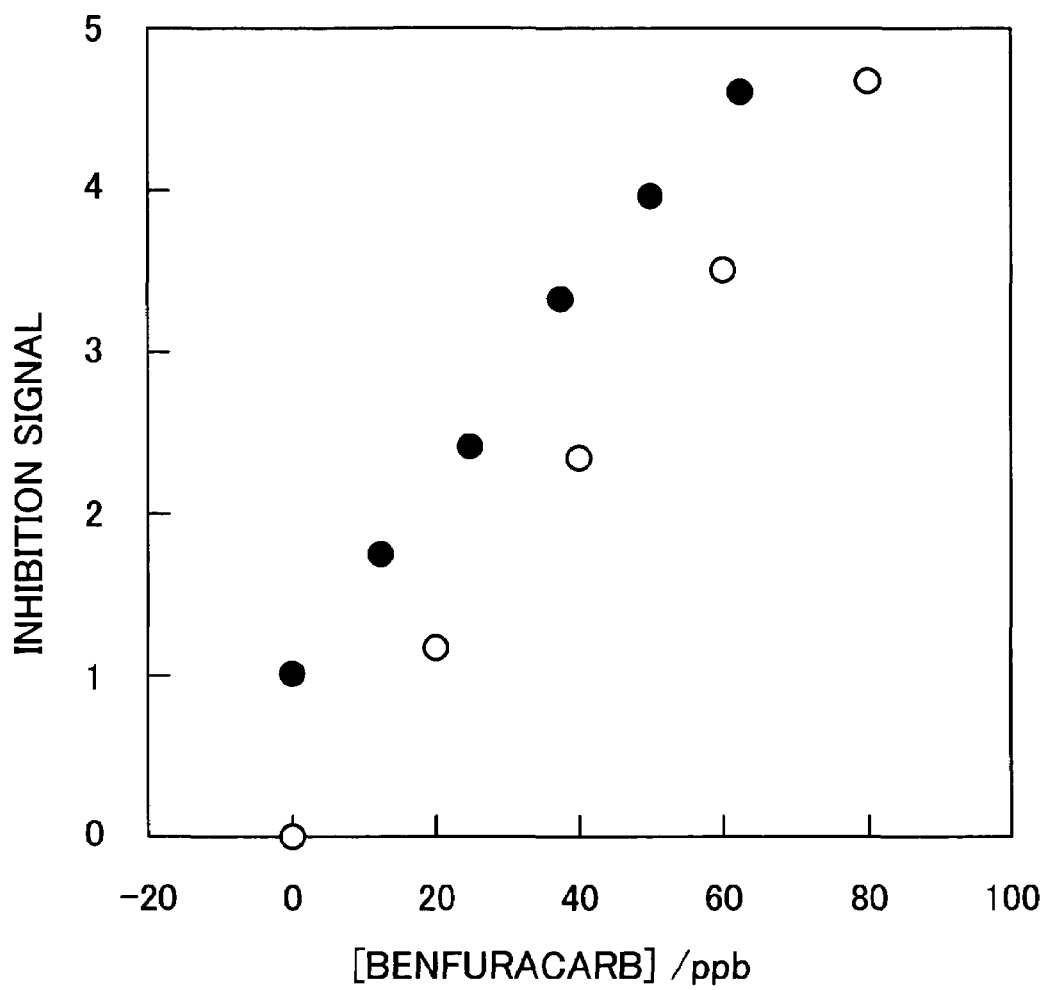
FIG. 5 is a calibration curve for the analysis of benfuracarb present in a sample (brown rice) to be examined.

In FIG. 5, the concentration of the agricultural chemical is plotted as abscissa and the inhibitory signal as ordinate. The curve represented by open circles (○) corresponds to the calibration curve obtained by the same method used in Example 1 in which a reference material for benfuracarb was converted into carbofuran with a reduced glutathione (GSH) and a glutathione transferase and that represented by filled circles (●) is the calibration curve obtained when adding 20 ppb of benfuracarb to brown rice, recovering the same, further adding benfuracarb to each test sample thus recovered in a variety of concentrations and then converting the agricultural chemical with a reduced glutathione and a glutathione transferase. The data plotted on FIG. 5 clearly indicate that the gradients of these two curves are identical to one another and that benfuracarb present in a test sample (brown rice in this case) can accordingly be derivatized into a desired product. Moreover, the intersection of the calibration curve represented by filled circles (●) and the abscissa corresponds to approximately −20 ppb and this indicates that the benfuracarb added to the sample immediately after the pulverization thereof can surely be recovered. Consequently, the results of the foregoing analysis of benfuracarb in the test sample (brown rice) clearly demonstrate that the method of the present invention permits the detection thereof with a sufficient detection sensitivity while comparing the same with the standard level for the residual agricultural chemical in the order of 0.2 ppm.

As has been discussed above in detail, the method of the present invention may serve as a powerful tool for the detection of the residual agricultural chemicals in grains such as rice and the detection of the content of agricultural chemicals remaining in agricultural products such as vegetables and fruits.

What is claimed is:

1. A method for detecting a residual agricultural chemical, comprising
    reacting reduced glutathione with the residual agricultural chemical, in the presence of a glutathione transferase, to form a choline esterase inhibitor,
    reacting the choline esterase inhibitor with a choline esterase to alter the activity of the choline esterase, and
    detecting the presence of the residual agricultural chemical based on changes in the choline esterase activity;
    wherein the residual agricultural chemical is selected from the group consisting of carbosulfan, furathiocarb, benfuracarb, thiodicarb and alanicarb;
    wherein the choline esterase inhibitor is selected from the group consisting of carbofuran and methomyl;
    wherein the reacting of the residual agricultural chemical with the reduced glutathione is conducted in the presence of a chelating agent, at a temperature ranging from 10° C. to 40° C., at a pH ranging from 5.0 to 8.5, and for a time period ranging from 5 to 60 minutes; and
    wherein the chelating agent is selected from the group consisting of EDTA and citric acid.

2. The method of claim 1, wherein the residual agricultural chemical is selected from the group consisting of carbosulfan, benfuracarb, and furathiocarb, and
    wherein the choline esterase inhibitor is carbofuran.

3. The method of claim 1, wherein the residual agricultural chemical is selected from the group consisting of alanicarb and thiodicarb, and
    wherein the choline esterase inhibitor is methomyl.

4. The method of claim 1, wherein the residual agricultural chemical is obtained from a sample, and wherein the sample is selected from the group consisting of rice, a vegetable, and a fruit.

5. The method of claim 4, wherein the sample is rice.

6. The method of claim 5, wherein the rice is brown rice.

7. The method of claim 4, wherein the sample is a fruit.

8. The method of claim 4, wherein the sample is a vegetable.

9. The method of claim 1, wherein the reacting the reduced glutathione with the residual agricultural chemical is conducted at a pH ranging from 6.0 to 7.0.

10. The method of claim 1, wherein the residual agricultural chemical is carbosulfan, and the choline esterase inhibitor is carbofuran.

11. The method of claim 1, wherein the residual agricultural chemical is benfuracarb, and the choline esterase inhibitor is carbofuran.

12. The method of claim 1, wherein the residual agricultural chemical is furathiocarb, and the choline esterase inhibitor is carbofuran.

13. The method of claim 1, wherein the residual agricultural chemical is alanicarb, and the choline esterase inhibitor is methomyl.

14. The method of claim 1, wherein the residual agricultural chemical is thiodicarb, and the choline esterase inhibitor is methomyl.

15. The method of claim 1, wherein the chelating agent is EDTA.

16. The method of claim 1, wherein the chelating agent is citric acid.

* * * * *